United States Patent [19]

Murray

[11] Patent Number: 4,466,435
[45] Date of Patent: Aug. 21, 1984

[54] BONE CEMENT NOZZLE AND METHOD

[76] Inventor: William M. Murray, 145 Bryce Rd., Camp Hill, Pa. 17011

[21] Appl. No.: 299,410

[22] Filed: Sep. 4, 1981

[51] Int. Cl.³ .............................................. A61B 17/00
[52] U.S. Cl. ................. 128/303 R; 128/305; 128/92 E; 128/92 C; 3/1.9; 141/367; 141/312; 141/189; 604/278
[58] Field of Search ............... 128/92 R, 92 G, 92 C, 128/305, 83, 303 R, 92 E, 345, 325; 433/89, 90; 3/1.9, 1.91; 141/382, 367, 312, 125, 374, 89, 1; 401/261, 265; 425/465, 466, 87, 458; 604/104, 106, 107, 8-10, 278, 213, 96

[56] References Cited

U.S. PATENT DOCUMENTS

| | | | |
|---|---|---|---|
| 860,555 | 7/1907 | Middaugh | 433/90 |
| 3,050,066 | 8/1962 | Koehn | 128/325 |
| 3,459,175 | 8/1969 | Miller | 604/96 |
| 3,690,323 | 9/1972 | Wortman et al. | 604/8 |
| 3,815,599 | 6/1974 | Deyerle | 128/92 R |
| 3,889,665 | 6/1975 | Ling et al. | 128/92 G |
| 4,245,359 | 1/1981 | Stuhmer | 128/92 C |
| 4,274,163 | 6/1981 | Malcom et al. | 3/1.91 |
| 4,338,925 | 7/1982 | Miller | 128/92 E |

OTHER PUBLICATIONS

Pansky and House, Review of Gross Anatomy, Copyright 1969, pp. 92-93.
Cintor Orthopaedic Division, "The Cement Fixation System", 1980.
Howmedica, Inc. Orthopaedics Division, "The Exeter Cement Security System", 1980.
Zimmer-USA Advertisement.

Primary Examiner—Richard J. Apley
Assistant Examiner—Harry J. Macey
Attorney, Agent, or Firm—Thomas Hooker

[57] ABSTRACT

An improved bone cement nozzle and method for use in filling a long bone medullary canal with bone cement. The nozzle includes an expandable shield which scrapes the canal wall and pressurizes the cement as it enters the canal so that it flows into interstices in the bone.

27 Claims, 9 Drawing Figures

U.S. Patent  Aug. 21, 1984  Sheet 1 of 2  4,466,435
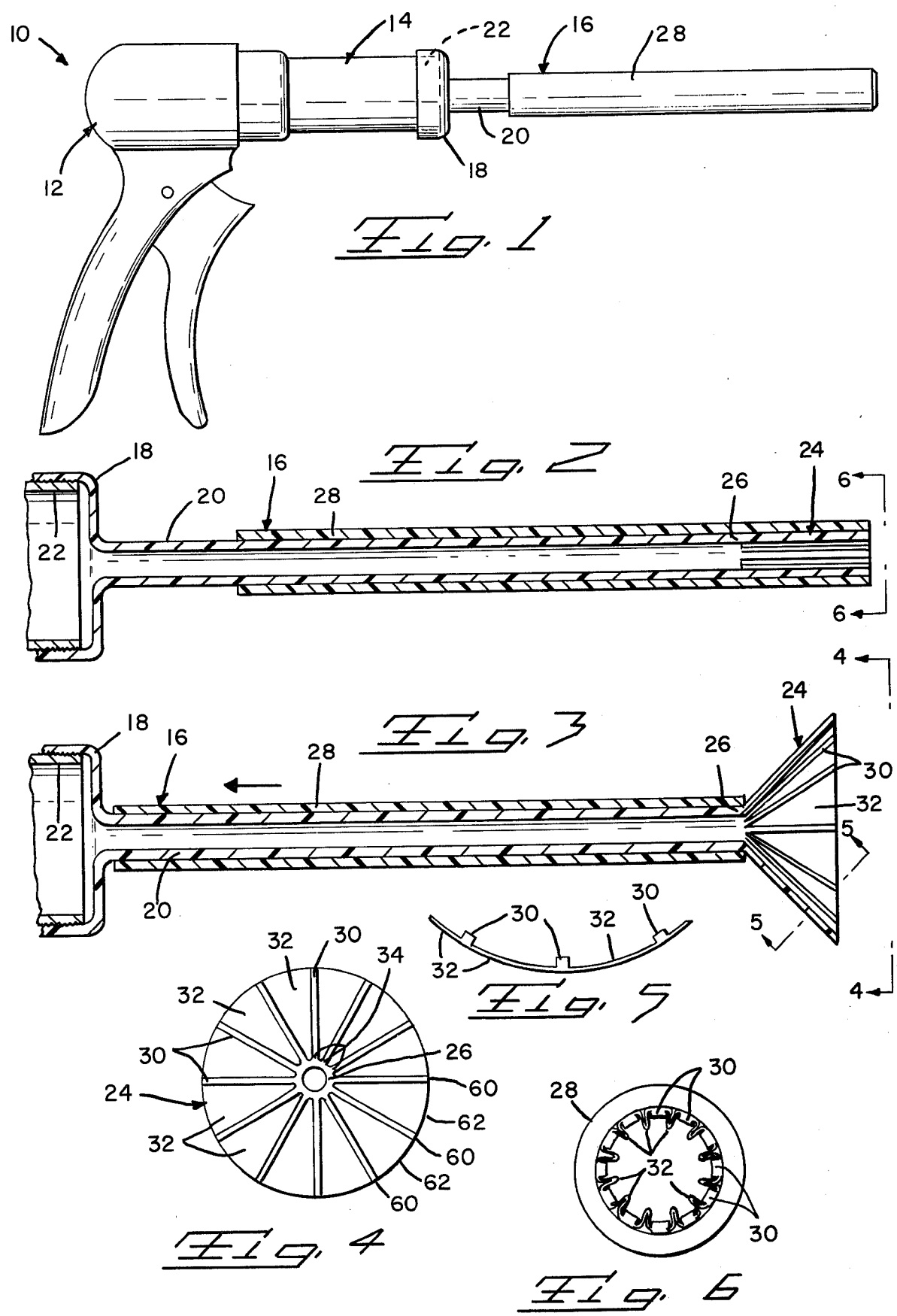

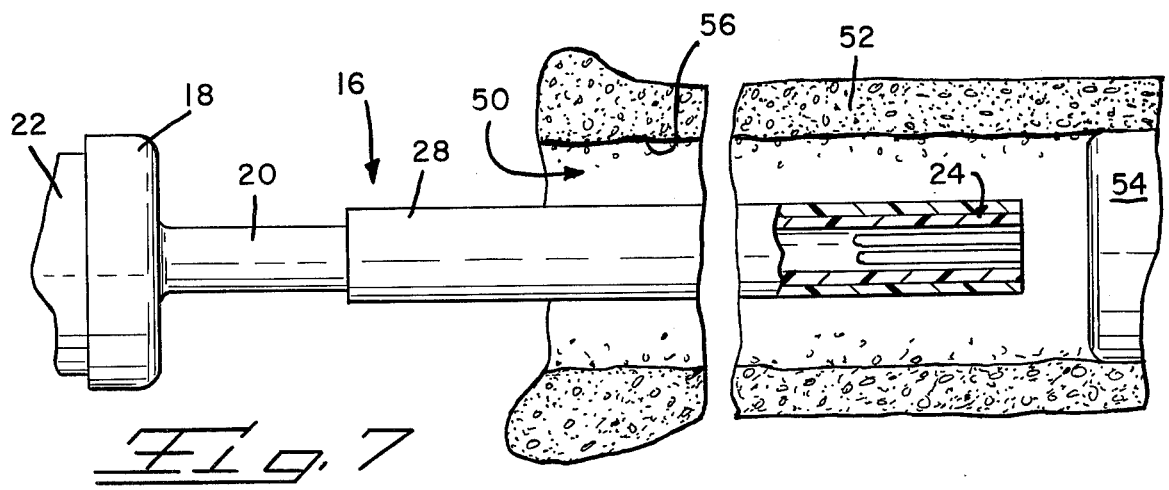
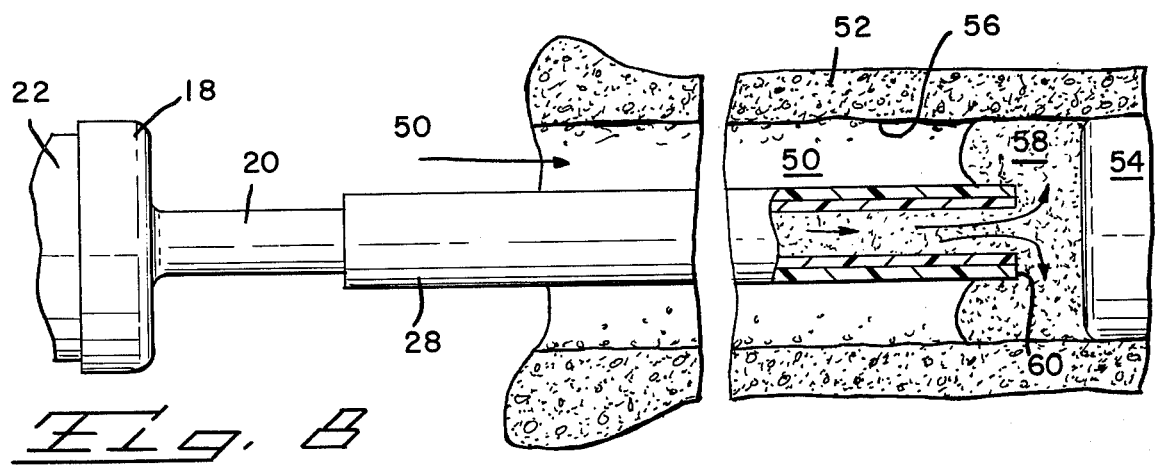
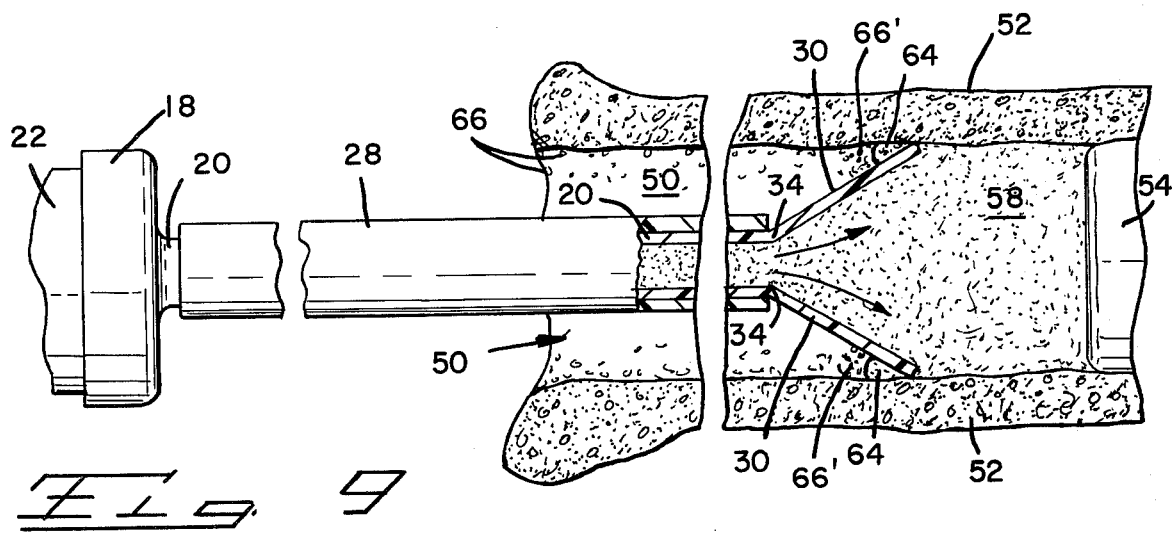

BONE CEMENT NOZZLE AND METHOD

The invention relates to an article and method for flowing bone cement into a long bone medullary canal prior to implanting of a prosthesis stem in the canal.

Prostheses are implanted in human and veterinary science patients, usually to replace worn or injured bone joints. Fast setting methyl methacrylate bone cement is used to form the connection between the prosthesis mounting stem and the surrounding cortical shaft. Successful implantation of a prosthetic device within a medullary canal using bone cement requires a strong bond be formed between the cement and the cortical shaft.

The bone is prepared for a prosthesis by first amputating the natural joint member and then carefully removing soft tissue from the exposed canal a distance along the canal sufficient to receive the stem of the prosthesis. After soft tissue has been removed, the canal is carefully irrigated and an attempt is made to clean away remaining soft tissue, blood and bone debris.

Following cleaning of the medullary canal, the surgeon plugs the bottom of the canal, mixes methyl methacrylate cement and prepares the cement gun for discharge of cement into the canal. The cement gun cartridge includes a long nozzle which is extended into the canal just short of the plug. Actuation of the cement gun flows cement into the canal. The nozzle is withdrawn along the canal as it is filled with cement. After the canal has been completely filled, the cement gun and nozzle are removed and a compacter is applied to the proximal end of the filled cavity to pressurize the cement within the canal and improve the flow of cement into the cortical shaft. The plug prevents cement from flowing beyond the cleaned portion of the medullary canal. Implantation of the prosthesis is completed by extending the prosthesis stem into the cement within the canal before the cement hardens.

One of the requirements for a successful bone prosthesis implant is that the connection between the prosthesis and the natural bone be strong enough to transmit stresses and strains of the magnitude transmitted by natural bone without loosening. In practice, long bone prostheses implanted by the described conventional technique fail because of loosening of the connection between the cement and the surrounding cortical shaft. This loosening is believed to occur as a result of a number of factors which prevent the cement, while viscous, from flowing fully into the interstices of the surrounding bone.

The final cleaning of the medullary canal is completed before the surgeon mixes the bone cement and prepares the cement gun for injecting cement into the canal. During this period, blood continues to flow through the live bone and into the canal to form blood clots on the interior surface of the cortical shaft. The clots on the shaft prevent the cement flowed into the canal from making maximum intimate contact with the bone and flowing into the bone interstices. The resultant cement-bone joint is weak.

Methyl methacrylate bone cement has a working time of only a few minutes after mixing is begun. The viscosity of the bone cement increases during the working time until, ultimately, the cement hardens and is unworkable. By the time the medullary canal has been fully filled with cement and a pressurizer is applied to pressurize the cement within the canal, the cement may have polymerized sufficiently to prevent the pressure applied at the end of the canal from forcing the cement into the bone interstices. Delay in the operative procedure means the cement will have a higher viscosity when the canal is pressurized with a resultant decreased flow of cement into the bone interstices. A weak joint will result.

The present invention is a bone cement nozzle and method for improving the bone-cement connection. The nozzle is attached to the end of a conventionally filled cement gun and is then inserted into a reamed, cleaned and plugged medullary canal with the end of the nozzle adjacent the plug. A shield on the end of the nozzle is released and expands within the canal. The shield includes a plurality of circumferentially spaced ribs with flexible webbing between the ribs.

When opened, the shield has a frustoconical shape with the minor circumference joining the end of the nozzle delivery tube and the major circumference bearing against the surface of the bone. The shield is flexible so that contact is maintained with the bone despite irregularities in the surface of the bone.

Cement flowed into the bottom of the medullary canal holds the shield open against the bone and forces the shield out against the side of the canal so that the edge scrapes closely along the canal and removes blood clots, bone fragments and other debris. Clots, bone fragments and debris are carried along the surface of the bone on the leading side of the shield. In this way, the surface of the cortical shaft is cleaned immediately prior to flowing cement against the bone to provide a clean, large-area bone-cement contact. The flowing of cement behind the shield and into the medullary canal automatically expels the nozzle along the canal while maintaining the desired scraping contact between the shield and the bone. The cement in the canal may be pressurized by resisting expulsion of the bone gun and nozzle. In this way, the bone cement is pressurized into the bone as soon as it is forced into the canal before it becomes more viscous.

Use of the invention in filling a medullary canal with bone cement eliminates the step or pressurizing the cement in the filled canal. Cement is pressurized as the canal is filled and the prosthesis stem may be inserted immediately into the filled canal. The need for a special tool for pressurizing the cement is eliminated. The surgeon has additional time to complete insertion of the prosthesis before the cement hardens and is no longer workable.

Other objects and features of the invention will become apparent as the description proceeds, especially when taken in conjunction with the accompanying drawings illustrating the invention, of which there are two sheets and one embodiment.

IN THE DRAWINGS

FIG. 1 is a side view of a bone cement dispenser with the nozzle according the invention;

FIG. 2 is a sectional view through the nozzle of FIG. 1;

FIG. 3 is a view like that of FIG. 2 with the shield open;

FIG. 4 is an end view taken along line 4—4 of FIG. 3;

FIG. 5 is a sectional view taken along line 5—5 of FIG. 3;

FIG. 6 is a sectional view taken along line 6—6 of FIG. 2; and

FIGS. 7, 8 and 9 are views illustrating the use of the nozzle in filling a medullary canal with bone cement.

Bone cement dispenser 10 includes a conventional bone cement extrusion gun 12 and a bone cement cartridge 14 with specialized extrusion nozzle 16. The nozzle 16 includes a cap 18 and central delivery tube 20 communicating with the interior of the cap. The cap 18 is conventionally mounted on the end of the cartridge 22 away from gun 12.

An expandable shield 24 is provided on the end 26 of tube 20 away from cap 18. A collar 28 surrounds tube 20 and, as illustrated in FIG. 2, extends outwardly overlying shield 24 to retain the shield in the collapsed position. Movement of the collar toward cap 18 uncovers the shield and allows it to expand as shown in FIG. 3. The cap 18, tube 20 and shield 24 may be formed of plastic material. The collar 28 may also be formed of plastic.

Shield 24 includes a numuber of circumferentially spaced, relatively rigid ribs 30 interconnected by imperforate flexible sheeting 32 between adjacent ribs. The inner ends of the ribs 30 join the end 26 of delivery tube 20 at flexible connections 34 which permit movement of the ribs from the collapsed position of FIG. 2 where the ribs extend parallel to the axis of delivery tube 20 to the fully open or expanded position of FIG. 3. In the fully open position, the ribs diverge outwardly from the axis of tube 20, and the sheeting 32 is taut between adjacent ribs.

When open, the shield assumes a generally truncated conical shape surrounding delivery tube end 26. In the collapsed position of the shield, as illustrated in FIG. 6, the sheeting 32 is folded between adjacent ribs within the interior of the collar.

During manufacture of the tube and shield, the ribs may be in the fully or partially open position. When the shield is collapsed, the ribs are against the collar. Upon withdrawal of the collar from the position of FIG. 2 to that of FIG. 3, the ribs snap out and the shield automatically opens.

The nozzle 16 is used for dispensing bone cement into a long bone medullary canal. After the canal is filled, the stem of a prosthetic element is inserted into the canal so that the cement forms a bond between the element and the bone. The element conventionally cooperates with another element secured to an adjacent bone to form an artificial joint. In orthopedics and veterinary science, prostheses are conventionally cemented to long bones using well established surgical procedures. The preferred procedure relating to preparation of the canal and introduction of the bone cement into the canal using nozzle 16 will now be described.

In FIGS. 7 through 9, the medullary canal 50 of long bone 52 has been prepared to be filled with bone cement prior to seating of the stem of a prosthetic element within the canal. The preparation includes amputation of the structure at one end of the bone, removal of the soft tissue within the canal, cleaning of the canal and insertion of a plug 54 in the bottom of the prepared canal.

After the canal has been cleaned and plugged, the surgeon prepares the bone cement for injection into the canal by mixing the ingredients and then loading the cement gun. Conventionally, bone cement is a fast setting methyl methacrylate composition. The viscosity of the bone cement increases rapidly after initial mixing.

During the time the medullary canal is being prepared and the surgeon is mixing the bone cement and loading the bone cement gun, blood continues to flow through bone 52 and clot on to surface 56. If allowed to remain on the surface when the medullary canal is filled with cement, the blood would undesirably weaken the connection between the cement and the bone.

When the cement gun is prepared, nozzle 16 is inserted into the canal as shown in FIG. 7 with the end of the nozzle positioned a short distance from plug 54. During insertion, collar 28 is extended to hold the shield 24 in the collapsed position. The gun 12 is then actuated to extrude a small portion of cement 58 into the bottom of the medullary canal, against plug 54 and up along the surface 56 a short distance past the extended end 60 of cover 28. See FIG. 8. The surgeon then draws the collar 28 toward cap 18 to uncover shield 24 while continuing to extrude bone cement into the medullary canal. The ribs 30 spread radially outwardly and the collapsed sheeting 32 opens as the shield expands until the ends of the ribs and sheeting 60 and 62 (see FIG. 4) contact the irregularly shaped interior surface 56. Opening of the shield in this manner traps an annular bead of bone cement 64 ahead of the shield between the end of the shield and the surface 56. The bead aids in forming a tight seal between the shield and the bone 52 and prevents air from being trapped behind the shield.

Withdrawal of the collar permits the prestressed ribs to automatically partially open the shield. The pressure of the bone cement behind the imperforate shield fully opens the shield and holds it against surface 56. The pressure of the bone cement forces the shield open when the ribs are not prestressed. In this case, the connections 34 may be weakened to permit ready flexing of the ribs about tube 20.

The gun 12 flows pressurized bone cement into the space beneath the shield, pressurizing the cement against the surface 56 as it flows into the canal so that the cement is immediately forced into interstices in the bone. As the gun continues to flow cement into the bottom of the canal, the pressurized cement acting on the interior surface of the shield biases the shield against the canal surface 56 and expels the gun and nozzle toward the proximal end of the canal. The shield moves along surface 56 and scrapes away any blood clots or other foreign matter 66' not previously cleaned from the canal. In this way, the shield assures that the surface 56 is fully cleaned immediately before the cement is forced into the bone. The pressure of the bone cement behind the shield may be controlled by the surgeon by increasing or decreasing the force resisting expulsion of the gun from the canal.

When the canal has been completely filled and shield 24 reaches end 66, the surgeon collects and removes the debris on the leading or outer surface of the shield, removes the shield from the cavity 50 and removes any excess bone cement. The surgeon then inserts the stem of the prosthetic device within the filled canal 50 in a conventional manner.

A given size shield 24 may be used to fill medullary canals of different diameters. After the nozzle has been inserted into the canal as shown in FIG. 8, withdrawal of the collar 28 allows the nozzle to expand from a closed position until the edge of the ribs and sheeting 60 and 62 contact the surface 56, whether the surface is relatively close to the nozzle or spaced further away from the nozzle. In order to assure the shield has sufficient capability to conform to the irregularities in surface 56, the maximum diameter medullary canal for a given sized nozzle should be slightly less than the maximum nozzle diameter as shown in FIGS. 7 through 9.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim my invention is:

1. A bone cement delivery nozzle for flowing bone cement into a long bone medullary canal, the nozzle including a delivery tube, first means at one end of the delivery tube adapted to be attached to a source of bone cement, wherein the improvement comprises a collapsible imperforate bone cement shield, a connection joining the shield to the other end of the delivery tube such that the shield is movable between a collapsed position for insertion into the canal and an expanded position when in the canal, the other end of the tube opening through the shield, the shield when expanded including a flexible outer circumferential portion engagable with the interior of the canal and an interior pressure surface impervious to bone cement facing the bottom of the canal, and second means for holding the shield in the collapsed position during insertion into the canal and permitting movement of the shield to the expanded position following insertion, whereby bone cement flowed through the tube, past the expanded shield and into the bottom of the canal contacts the interior pressure surface of the shield, biases the outer portion of the shield against the canal and expels the nozzle outwardly of the canal thereby cleaning the canal.

2. A nozzle as in claim 1 wherein the shield has a generally truncated conical shape when expanded.

3. A nozzle as in claim 1 wherein the shield includes stiffening members extending from the other end of the delivery tube to the portion.

4. A nozzle as in claim 1 wherein said second means includes an operator for releasing the shield for movement from the collapsed position to the expanded position after insertion of the shield into a medullary canal.

5. A nozzle as in claim 1 wherein said shield includes a plurality of circumferentially spaced ribs extending from the other end of the delivery tube to said portion, flexible sheeting between the ribs and said connection includes hinge connections joining the ribs to the other end of the delivery tube to permit movement of the ribs with respect to the tube as the shield moves from the collapsed to the expanded position.

6. A nozzle as in claim 5 wherein when collapsed, said ribs and hinges are biased toward the open position.

7. A nozzle as in claim 5 wherein when the shield is collapsed the ribs extend parallel to the axis of the delivery tube and the sheeting between adjacent ribs is folded.

8. A nozzle as in claim 7 wherein when the shield is collapsed the sheeting between adjacent ribs is folded inwardly toward the axis of the delivery tube.

9. A nozzle as in claim 8 including means engageable adjacent to the one end of the delivery tube for releasing the shield for movement from the collapsed position to the expanded position after insertion of the shield into a medullary canal.

10. A nozzle as in claim 9 wherein said means comprises a member slidable along said delivery tube and including a ring surrounding the shield when collapsed.

11. A nozzle as in claim 10 wherein said member comprises an elongate collar slidably mounted on said delivery tube.

12. A nozzle for flowing bone cement into a prepared long bone medullary canal, the nozzle having a delivery tube, first means at one end of the tube adapted to be attached to a source of bone cement and the other end adapted to be extended into a medullary canal, wherein the improvement comprises an imperforate flexible shield impervious to bone cement secured to the other end of the delivery tube, the shield including a plurality of circumferentially spaced ribs joined to and projecting beyond the other end of the delivery tube with flexible sheeting extending between adjacent ribs from the delivery tube to an outer edge of the shield, said ribs being moveable between a collapsed position where they lie generally parallel to the axis of the tube and the sheeting between adjacent ribs is folded and an expanded position where the ribs extend outwardly of the delivery tube, the outer surface of the shield circumferentially engages the wall of the medullary canal and the ribs and sheeting define an interior shield pressure surface facing the bottom of the canal, and second means operable for controlling movement of the shield from the collapsed position to the expanded position after insertion of the shield into the medullary canal.

13. A nozzle as in claim 12 wherein when the shield is collapsed the sheeting is folded inwardly toward the axis of the delivery tube.

14. A nozzle as in claim 12 wherein when the shield is collapsed said ribs are prestressed toward the open position.

15. A nozzle as in claim 12 wherein said hinge connection is weakened to permit free movement of the sides relative to the delivery tube.

16. A nozzle as in claim 12 wherein said second means comprises a collar slidably mounted on the delivery tube, one end of the collar overlying the shield when collapsed whereby movement of the other end of the collar away from the shield releases the shield for movement toward the expanded position.

17. A nozzle as in claim 16 wherein said delivery tube and shield are formed of an body of plastic material.

18. The method of filling the medullary canal of a live long bone with bone cement comprising the steps of:
  a. Freely introducing a collapsed bone cement shield into the canal;
  b. Expanding the shield within the canal;
  c. Flowing bone cement through the shield to fill the canal beyond the shield and bias the edge of the shield into contact with the surface of the canal;
  d. Moving the edge of the shield outward along the surface of the canal to clean the surface of blood and any debris; and
  e. Flowing bone cement into the interstices of bone cleaned by the edge of the shield.

19. The method of claim 18 including the step of opening the shield and flowing bone cement past the shield without forming air voids in the cement.

20. The method of claim 18 including the steps of flowing a small portion of bone cement into the canal after insertion of the collapsed shield into the canal so that the cement fills the bottom of the canal and extends past the end of the shield and opening the shield so that the edge opens into the cement to form a bead of cement ahead of the shield between the edge and the surface of the canal.

21. The method of claim 18 including the step of flowing cement through the shield to move the shield along the medullary canal.

22. The method of claim 18 including the step of forming an annular bead of bone cement ahead of the shield between the shield edge and the surface of the canal.

23. The method of claim 18 including the step of flowing bone cement into interstices of bone in the surface of the medullary canal immediately after the bone has been cleaned of blood and debris by the sheild.

24. The method of claim 18 including the step of maintaining the edge of the shield in contact with the surface of the medullary canal despite variation in the diameter of the canal along its length.

25. The method of filling the medullary canal of a live, long bone with bone cement comprising the steps of:
 a. Freely introducing a bone cement shield into the canal;
 b. Expanding the shield within the canal so that the shield engages a circumferential band of the canal surface and forms a barrier in the canal; and
 c. Flowing cement through the shield and into the canal thereby forcing the shield outwardly of the canal as it is filled with cement while maintaining contact between the shield and the canal surface to clean the surface of the canal and collect the matter cleaned from the surface on the exterior side of the shield.

26. The method of claim 25 including the step of initially flowing bone cement through the shield, into the canal and past the free end of the shield to form a circumferential bead of cement on the wall of the medullary canal in front of the shield when expanded.

27. The method of claim 26 including the step of removing air from the end of the medullary canal to be filled with cement prior to opening the shield against the wall of the canal.

* * * * *

UNITED STATES PATENT AND TRADEMARK OFFICE
CERTIFICATE OF CORRECTION

PATENT NO. : 4,466,435
DATED : August 21, 1984
INVENTOR(S) : William M. Murray

It is certified that error appears in the above—identified patent and that said Letters Patent is hereby corrected as shown below:

Column 2, line 43 change "or" to --of--.

Column 5, line 53 change "open" to --expanded--.

Column 6, line 5 change "nozle" to --nozzle--.

Signed and Sealed this

Twenty-sixth Day of February 1985

[SEAL]

Attest:

DONALD J. QUIGG

*Attesting Officer*  *Acting Commissioner of Patents and Trademarks*